United States Patent
Matthews

(10) Patent No.: US 9,325,637 B2
(45) Date of Patent: *Apr. 26, 2016

(54) SYSTEM FOR PERFORMING DISTRIBUTED DATA CUT-THROUGH

(75) Inventor: Brad Matthews, San Jose, CA (US)

(73) Assignee: Broadcom Corporation, Irvine, CA (US)

( * ) Notice: Subject to any disclaimer, the term of this patent is extended or adjusted under 35 U.S.C. 154(b) by 445 days.

This patent is subject to a terminal disclaimer.

(21) Appl. No.: 13/611,252

(22) Filed: Sep. 12, 2012

(65) Prior Publication Data

US 2013/0322244 A1 Dec. 5, 2013

Related U.S. Application Data

(63) Continuation of application No. 13/564,118, filed on Aug. 1, 2012.

(60) Provisional application No. 61/654,384, filed on Jun. 1, 2012.

(51) Int. Cl.
*H04L 12/26* (2006.01)
*H04L 12/947* (2013.01)

(52) U.S. Cl.
CPC .......... *H04L 49/251* (2013.01); *H04L 12/2676* (2013.01)

(58) Field of Classification Search
None
See application file for complete search history.

(56) References Cited

U.S. PATENT DOCUMENTS

| | | | |
|---|---|---|---|
| 6,721,273 B1 * | 4/2004 | Lyon | 370/235 |
| 7,843,846 B1 | 11/2010 | Dropps et al. | |
| 2005/0030948 A1 | 2/2005 | Wyatt | |
| 2005/0271073 A1 | 12/2005 | Johnsen et al. | |
| 2010/0265821 A1 * | 10/2010 | Schmidt et al. | 370/230 |

OTHER PUBLICATIONS

U.S. Office Action, dated Jul. 7, 2014, pp. 1-12, issued in U.S. Appl. No. 13/564,118, U.S. Patent and Trademark Office, Alexandria, VA.

* cited by examiner

*Primary Examiner* — Rhonda Murphy
(74) *Attorney, Agent, or Firm* — Brinks Gilson & Lione

(57) ABSTRACT

A system for transferring data includes an egress node including an egress port, and an ingress node configured to receive a data segment of a data packet destined for the egress port. The data packet is associated with a packet priority level. The ingress node is configured to receive an egress statement vector from the egress node indicating whether the egress port is or is not flow controlled for data associated with the packet priority level. The ingress node is configured to determine whether the egress port is available to receive the data segment from the ingress node before other data segments of the data packet are received at the ingress node based on the egress statement vector.

20 Claims, 10 Drawing Sheets

$$ICT_{MN} = \begin{bmatrix} 1 & 0 \\ 0 & 0 \\ 0 & 1 \\ 0 & 0 \end{bmatrix}$$

Figure 6

SYSTEM FOR PERFORMING DISTRIBUTED DATA CUT-THROUGH

1. RELATED APPLICATIONS

The present patent application is a continuation application of U.S. patent application Ser. No. 13/564,118, filed Aug. 1, 2012, and claims the benefit of the filing date under 35 U.S.C. §119(e) of provisional U.S. patent application Ser. No. 61/654,384, filed Jun. 1, 2012, both of which are hereby incorporated by reference.

2. TECHNICAL FIELD

This disclosure relates to systems and methods (generally referred to as systems) for transferring data. More specifically, this disclosure relates to a system for performing cut-through switching or data transfer.

3. BACKGROUND

Data and other information may be transmitted from one or more ports, nodes, locations, or devices to one or more other ports, nodes, locations, or devices. In some instances, a switching system or network switch may be used to facilitate the transfer of data between ports, nodes, locations or devices.

BRIEF DESCRIPTION OF THE DRAWINGS

The innovation may be better understood with reference to the following drawings and description. In the figures, like reference numerals designate corresponding parts throughout the different views.

FIG. 6 is a diagram of an exemplary ingress cut-through statement vector.

DETAILED DESCRIPTION

With increasing technology and data transfer demands, emerging cloud network customers may benefit from high bandwidth aggregation devices for their networks. In addition to high bandwidth aggregation, a desirable system may have low latency data delivery. Latency may determine or reflect responsiveness and quality of results a user sees, or impact the revenue for the provider of the Internet service. As such, a system which provides high bandwidth aggregation and increased data delivery speeds may be useful.

Figure 1:
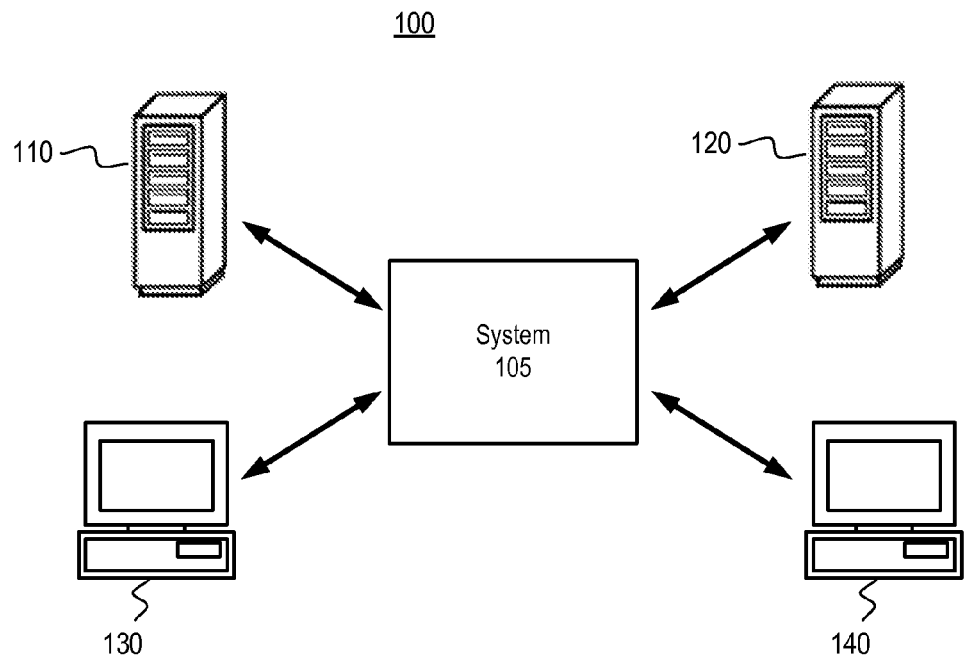
FIG. 1 is a block diagram of an exemplary network for transferring data.

FIG. 1 is a block diagram of an exemplary network 100 for transferring data. The network 100 may include various devices, such as one or more servers 110 and 120 and one or more computers 130 and 140. The network 100 may include a set of servers or a server bank. The network 100 may include a vast network of interconnected computers or network devices. The devices may be interconnected as part of a data center, or may be devices interconnected in an automotive environment. The network 100 may include one or more other devices, such as, for example, one or more wireless telephone, mobile device or mobile phone, smart phone, communications device, tablet, personal computer (PC), set-top box (STB), personal digital assistant (PDA), palmtop computer, laptop computer, desktop computer, land-line telephone, control system, camera, scanner, facsimile machine, printer, pager, personal trusted device, web appliance, network router, switch or bridge, or any other machine or device.

One or more systems, such as system 105, may be implemented to facilitate communication between the one or more devices of the network 100. Some or all of the devices of the network 100, such as some or all of the servers 110 and 120 and computers 130 and 140, may be connected or otherwise in communication with each other, through or using the system 105.

Figure 2:
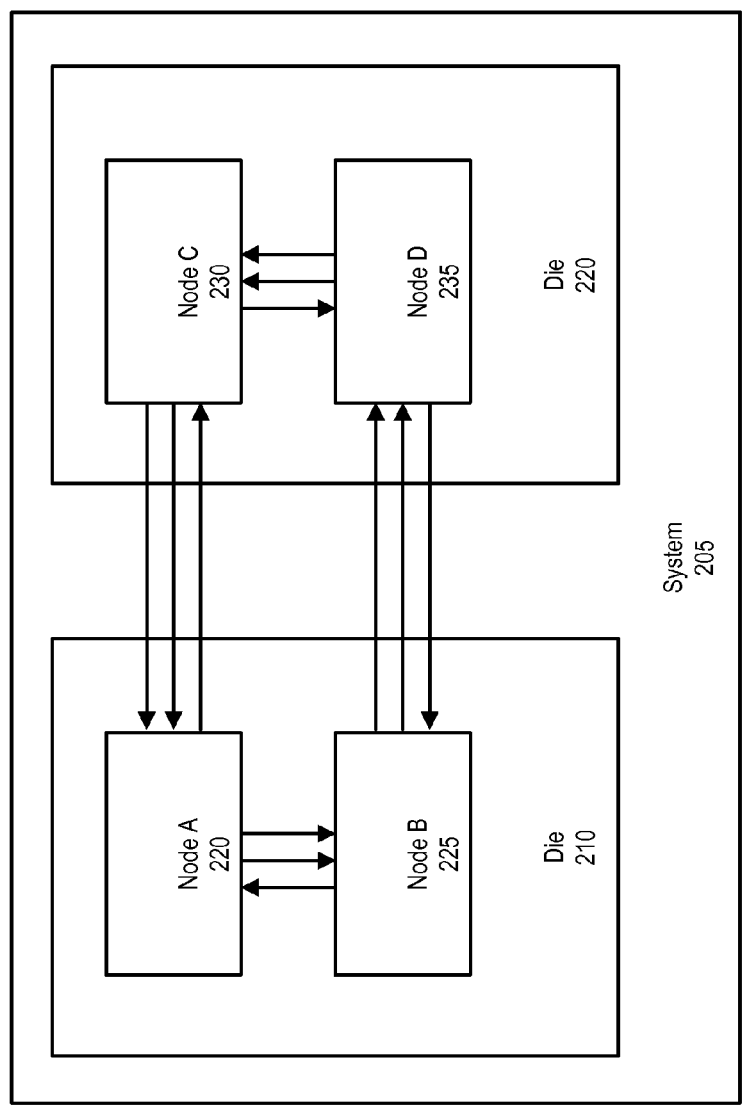
FIG. 2 is a block diagram of an exemplary system for transferring data.

FIG. 2 is a block diagram of an exemplary system 205 for transferring data. The system 205 may be similar to, the same as, or resemble the system 105. The system 205 may include one or more integrated circuits, chips, or dies 210 and 220. A die may refer to a block of semiconducting material, on which a given functional or integrated circuit may be fabricated. The dies 210 and 220 may include one or more tiles or nodes, such as node A 220 and node B 225 of die 210, and node C 230 and node D 235 of die 220. Systems, such as system 105 or 205, may have any number of dies, and dies may have any number of tiles or nodes. A node or tile may represent a single die in a chip. A node may refer to multiple chips in a device or system, or multiple devices in a system or chassis. A node may represent a single logical entity in one die. Some systems may include multiple die, where each die contains one or more nodes in a single chip or device. Some systems may additionally or alternatively include one or more chips or devices.

The nodes of the system 205 may include one or more ports. One or more devices, such as the servers 110 and 120 or computers 130 and 140, may connect or communicate with or through the system 205 using the one or more ports of the nodes. A node A 220 may have two ports, such that a server 110 may connect to a first port of the node A 220 and the server 120 may connect to the second port of node A 220. Nodes of a system may only have one port, or may have more than two ports. Ports may have a finite receive and transmit bandwidth, while a system 205 may have an aggregate bandwidth achieved by combining the bandwidth of the ports of the system. As an example, a system may have four ports with a bandwidth of 500 gigabits per second, and the system 205 may have an aggregate bandwidth of 2 terabits per second.

Ports of a system 205 may be internal on a single chip or die, or may be spread across multiple chips or dies. The system 205 may, in some instances, be similar to or resemble a network switch. The system 205 may have any number of nodes or ports.

Ports in a tile or node may be, for example, ingress ports or egress ports. Data, bits of data, a data packet, a set of data, signals, or a frame (referred to as "data" or "data packet") may arrive at or be received by the system 205 at or through an ingress port. In some instances, the data packets may be large, and may arrive and/or be processed in smaller pieces (sometimes referred to as data "cells," "segments," "chunks," or "portions"). The data packet may depart from the system 205 at or through an egress port. Other variations or port types are possible. Each die may contain one or more nodes or tiles. A device (such as a chip or package) may include one or multiple die. For example, a device may include two die, each die includes two tiles, such that the device includes four tiles. Other variations and examples are possible.

As an example, the server 110 may send a data packet to an ingress port of the node A 220 of the system 205, to be sent to the computer 130 connected with an egress port of the node B 225 of the system 205. The system 205 may transfer the data packet from the ingress port of node A 220 internally to the egress port of node B 225. The system 205 may transmit the data packet from the egress port of node B 225 to the server 120. Other variations and examples are possible.

Ingress ports and ingress nodes may transmit data to egress nodes or egress ports in various ways. In a store-and-forward data transfer, an ingress port may receive data segments of a data packet. The ingress port may store the data segments in memory or a buffer internally within the ingress port or ingress node until the entire data packet has been received. Once the data packet is received at the ingress port and the egress port it is destined for is available to receive the data, the ingress port may be authorized to transmit the stored data segments of the data packet from the internal memory of the ingress port or ingress node to the egress port. In a store-and-forward data transfer, all data segments may be stored before the egress port transmits the data packet.

In a cut-through data transfer, the ingress port may receive data segments of a data packet. In a cut-through data transfer, the ingress port may transmit the data segments to the egress port without storing the data segments in an internal buffer or memory of the ingress port or ingress node. In a cut-through data transfer, the egress port may transmit a portion of the packet prior to having fully received the packet from the ingress port. Data may be transferred by the ingress port to the egress port with a lower delay when the data is being transferred using a cut-through data transfer than if the data is transferred using a store-and-forward data transfer.

Cut-through data transfer may rely on a state and availability of the egress port that the data packet is destined for or is to be sent or transmitted to. Cut-through data transfer may only be possible when no other ingress ports in a system have data to be sent to the egress port and when the egress port is idle, available, or otherwise free to receive a data segment from an ingress port.

Ingress nodes or ingress ports may generate, create, determine, and/or otherwise use ingress cut-through statement vectors (sometimes referred to as "cut-through vectors," "cut-through statements," or "statement vectors"). An ingress cut-through statement vector (sometimes referred to as "ingress statements," "ingress statement vectors," or "ingress cut-through statements") may be a mathematical vector which may indicate whether the ingress node or ingress port generating the ingress cut-through statement vector has any data to be transmitted or otherwise sent to an egress port.

Egress nodes or egress ports may generate, create, determine, and/or otherwise use egress cut-through statement vectors (sometimes referred to as "egress statements," "egress statement vectors," or "egress cut-through statements"). An egress cut-through statement vector may be a mathematical vector which may indicate whether the egress node or egress port generating the egress cut-through statement vector is idle, available, or otherwise operable to receive data from an ingress node or ingress port. The control modules of the port or node may generate the cut-through statement vectors for the ports or nodes.

Ports or nodes may generate, create, determine, and/or otherwise use cut-through statement vectors to determine whether to use a cut-through data transfer or another type of data transfer, such as a store-and-forward data transfer. The ingress ports may receive, identify, and/or gather the ingress cut-through statements and the egress cut-through statements. The ingress nodes that receive and/or identify ingress cut-through statement vectors from other ingress nodes in the system may determine whether or not the other ingress nodes have any data to be sent or transmitted to an egress node or port. The ingress nodes that receive and/or identify egress cut-through statement vectors from egress nodes or egress ports may determine whether or not the egress nodes or ports are idle, available, or otherwise operable to receive data from an ingress node. Based on the cut-through statement vectors, the ingress node may determine that the ingress node may be authorized to transfer data using a cut-through data transfer. For example, the ingress node may determine that the ingress node is authorized to transfer data using a cut-through data transfer when the ingress cut-through statement vectors indicate no other ingress ports in a system have data to be sent to the egress port and when the egress cut-through statement vectors indicate the egress port is idle, available, or otherwise free to receive a data segment from an ingress port.

Figure 3:
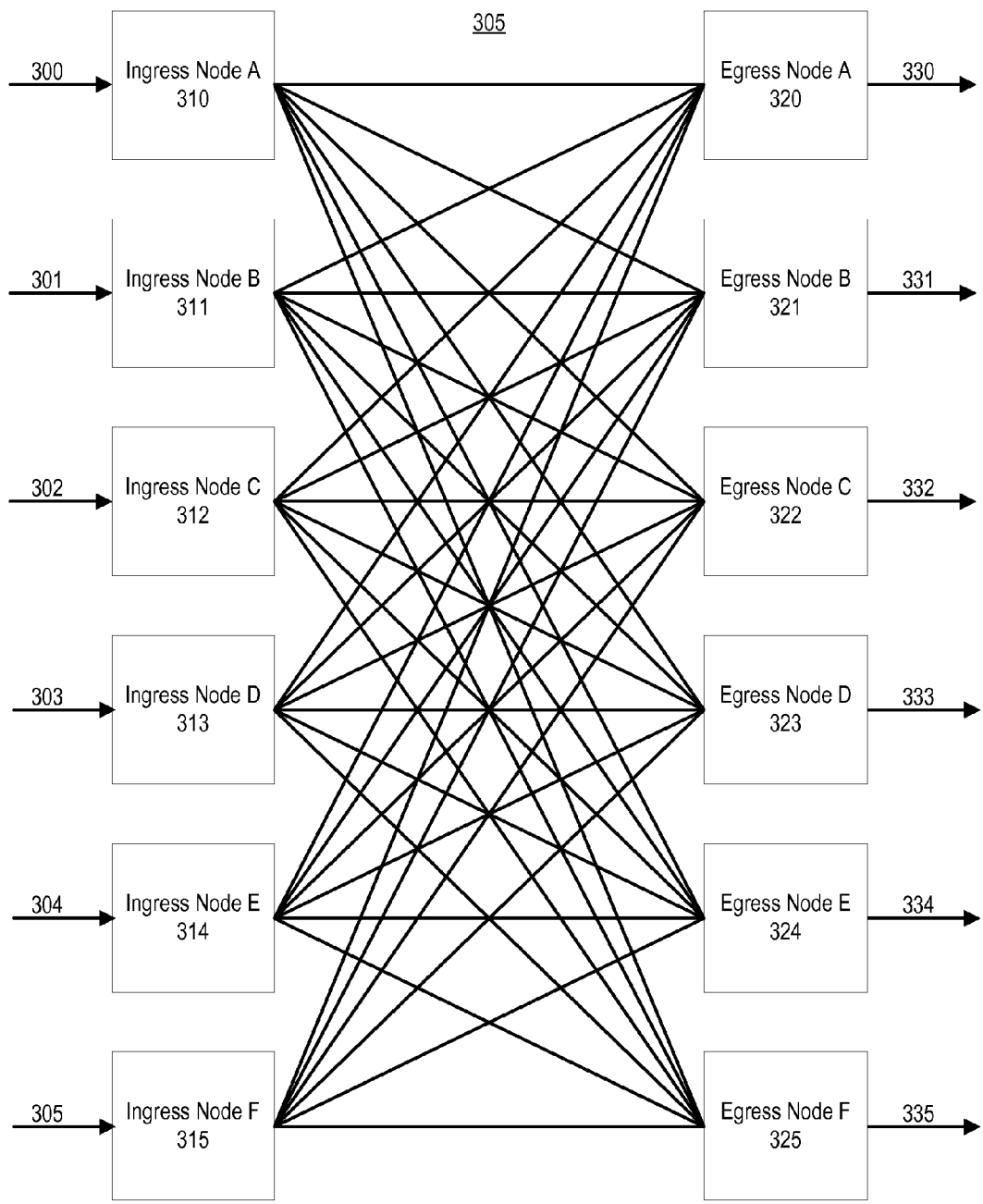
FIG. 3 is a block diagram of an exemplary system for transferring data.

FIG. 3 is a block diagram of an exemplary system 305 for transferring a data packet. The system 305 may be similar to, the same as, or different from the system 105. The diagram shows an example unfolded view of system 305 showing the interconnections of various nodes of a system, and may be referred to as a full mesh or fabric. Ingress nodes 310-315 may be able to communicate or be connected with the egress nodes 320-325.

For simplicity, the system 305 may be described assuming the ingress nodes 310-315 includes only one ingress port, and the egress nodes 320-325 includes only one egress port. However, it should be appreciated that the nodes 310-315 and 320-325 may include more than one port. Where one or more of the ingress nodes 310-315 (or egress nodes 320-325) include multiple ports, the ingress (or egress) nodes may be configured or operable to communicate with the ports of the egress (or ingress) nodes.

The system 305 may include six ingress nodes with ingress ports, such as ingress node A 310, ingress node B 311, ingress node C 312, ingress node D 313, ingress node E 314, and ingress node F 315, and six egress nodes, such as egress node A 320, egress node B 321, egress node C 322, egress node D 323, egress node E 324, and egress node F 325. In other variations, the system 305 may have more or less ingress nodes or egress nodes.

Ingress ports of the one or more of the ingress nodes 310-315 and egress ports of the one or more egress nodes 320-325 may be configured or operable to be connected with or in communication with one or more devices. The ingress ports associated with the ingress nodes 310-315 may be connected with a server in a bank of servers.

Nodes or tiles may be connected to devices, and may include both an ingress port and an egress port. A node may include or operate as both the ingress port and egress port and may be connected to one device.

The ingress ports of the ingress nodes 310-315 may be configured or operable to receive a signal, data packet or other information, such as data 300-305. An ingress port of the ingress node A 310 may be configured or operable to receive data 300 from a server connected with the ingress node A 310. An ingress port of the ingress node C may be configured or operable to receive data 302 from a server connected with the ingress port of the ingress node C 312.

A piece of received data 300-305 may be directed, destined, or otherwise intended for one or more egress ports, such as an egress port of any one of the egress node A 320, egress node B 321, egress node C 322, egress node D 323, egress node E 324, or egress node F 325. In some instances, the received data 300-305 may be directed, destined, or otherwise intended for one or more devices connected with the system 305 through one or more of the egress ports on the egress nodes 320-325. For example, data 300 may be sent by a device to an ingress port of ingress node A 310, and may be destined or intended to be transmitted or sent to an egress port of the egress node D 323 or a device connected to the system 305 through egress node D 323.

In some systems, the received data 300-305 may specify or include an identifier which may indicate which egress port of an egress node 320-325 that the data is directed to, destined for, or otherwise intended to be sent to. A received packet of data may contain information that may be used by packet processing logic or a packet processing unit in a node to resolve a destination node or port. For example, a first data segment of a data packet may include one or more labels or identifiers that may indicate the destination egress port for that data segment and some or all other data segments for that data packet. In other systems, the ingress port or ingress node that received the data 300-305 may perform one or more functions or algorithms to determine the egress port of the egress node 320-325 that the data is intended to be sent to. The data packet may be destined for one node or port, or may be a multicast packet that may have more than one destination node or port.

The ingress ports or ingress nodes 310-315 may process the received data 300-305, and may determine what egress port or egress node 320-325 that the data 300-305 should be sent to. The data packet may then be sent from the receiving ingress port or ingress node to the destination egress port or egress node that the data packet was intended for. In some systems, a data packet received at any ingress port of the ingress nodes 310-315 may be specified for, transmitted to, and/or otherwise sent to any of the egress ports of egress nodes 320-325 of the system 305. In other systems, a data packet received at some ingress ports may be restricted to transmission to only one or some of the egress ports. Other variations are possible.

The data packet may then be received by the destined egress port or egress node. The egress port or egress node 320-325 may perform one or more processes on the data, and then may output the data as output data 330-335 to one or more devices attached to the destination egress port of the egress node. Other variations and examples are possible.

A port may have one or more class of service, or priority level, associated with it. The class of services may have their own separate queues for data transfers to or from the port. As one example, a port may have 8 class of services, or priorities, each with a separate data queue. Other variations are possible.

Figure 4:
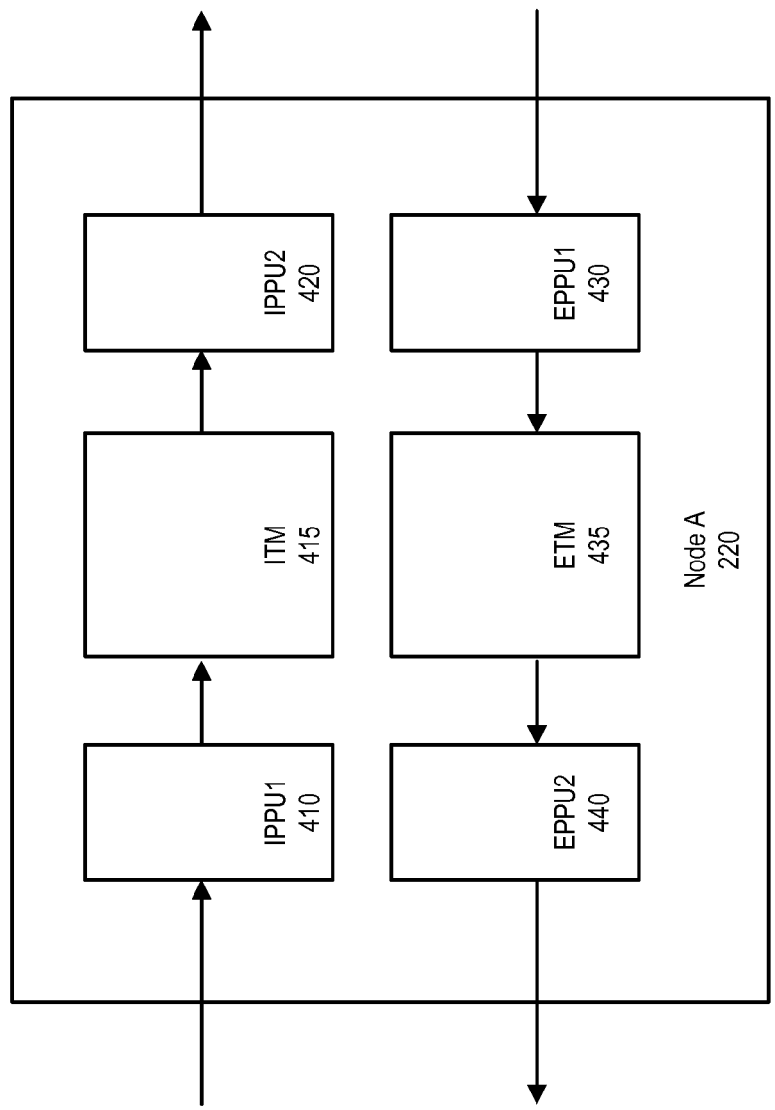
FIG. 4 is a block diagram of an exemplary node of a system for transferring data.

FIG. 4 is a block diagram of an exemplary node of a system for transferring data. The node A 220 in FIG. 4 may be the node A 220 of the system 205, and may operate to receive data packets from, or send data packets to, one or more other ports or nodes of the system 205 using a store-and-forward data transfer. The node A 220 may include, or operate as, one or both an ingress port and an egress port.

The system 205 may operate to transmit data packets between nodes and through the system 205 in various ways and using various data transfer types. In store-and-forward, a node of the system 205 may process data by storing segments of a data packet in a buffer or memory of the node or system 205 prior to transmitting the data packet from one node to another.

In store-and-forward, the node A 220 may be or operate as an ingress port and receive data packets from one or more devices connected or in communication with node A 220, such as at or through a network interface. For example, a node may have twelve ports configured to receive 1 gigabit of data per second. Other variations are possible.

The data packets received at the node A 220 may be specified as destined for one or more other node or ports of the system 205 (which may be referred to as "destination tiles," "destination nodes," "destination egress ports," or "destination ports"). A server 110 may be connected to an ingress port of the node A 220 of the system 205, and may transmit data to the ingress port of node A 220 to be transmitted to one or more other devices which may be connected with an egress port of a different node of the system 205, such as computer 130 attached to an egress port of node B 225. The destination node or destination port for the data may be the egress port of node B 225.

Packet processing may be performed upon receiving a packet by or with a packet processing unit ("PPU"), such as an ingress PPU ("IPPU") 1 410. IPPU1 410 may, for example, conduct an initial packet processing phase where the destination node(s) and/or port(s) may be determined or resolved. Afterwards, the data packets or segments may be forwarded to an ingress traffic manager ("ITM") 415.

The node A 220 may be ready to send or transmit data packet to an egress port of a node at various times and according to various conditions. For example, in some systems, data packets may be large, and may be received at the ingress port in data segments, which may be internally processed by the ingress port as they are received. In some instances, such as during some store-and-forward data transfers, the received data segments may be stored in the ITM 415 until all of the data segments of the data packet have been received and/or until the node is ready to send the data packet to an egress port. In some systems, the ingress port may perform one or more validity checks on the data packet prior to transmitting the packet. If the data packet is not valid, the ingress port may drop or not transmit the packet. In other instances, such as during some cut-through data transfers, data packets may not be stored in the ITM 415.

As another example, an ingress port of node A 220 may store received data segments, or entire data packets, within the ITM 415 until the egress port is ready to receive the data segments or data packets. Multiple ingress ports may have data packets to be sent to an egress port. In these, if the egress port is already receiving data from one ingress port, the egress port may not be configured or operable to receive data from the ingress port of node A 220. As another example, in some systems, an egress port may have data (such as store-and-forward data) it has received at a previous time or clock cycle, and may need to process or otherwise transmit the data to one or more devices. In some of these systems, the egress port may not be capable or operable to receive a data packet from the ingress port of node A 220. An egress port may additionally or alternatively be flow controlled or otherwise controlled to restrict the flow of data to the egress port (sometimes referred to as "data flow controlled"). An egress port may be flow controlled, for example, where a device that the egress port is connected or in communication with is full, congested, or otherwise cannot accept any more data, and alerts the egress port of this status. In some of these systems, the egress port may not be capable or operable to receive data from the ingress port of node A 220. Where an egress port has associated with it more than one class of services or priorities, the flow control of the egress port may be applied on a per class of service basis. For example, where the egress port has four class of services, the port may be flow controlled for the first class of service, and not flow controlled for the other three class of services. Other variations are possible.

In these and other systems, the data packet may be stored in the ITM 415 of the ingress port of node A 220 until the egress port is available to receive the data, such as when the egress port is idle. In some instances, the ingress port of node A 220 may not be ready to send the data packet until one or more combination of factors are satisfied, such when all of a data packet has been received and the egress port is ready to receive the data packet. Other variations are possible.

In store-and-forward, when the ingress port of node A 220 is ready to send or transmit the data packet stored in the ITM 415 to a destination egress port, the data packet may first be sent to one or more packet processing units which may perform additional processing on the data packet prior to the transmission to the egress port. For example, the data may first be sent to or passed through an IPPU2 420, which may perform one or more processes on the data. The data may then be transmitted after such additional processing to the destination egress port of the egress node of the system 205, such as by or through a tile fabric adaptor or other component. In other systems, the data packet may be ready to be transmitted without further packet processing.

The node A 220 may also be, include, or otherwise act as an egress port. A data packet which was sent or transmitted by a different port or node in the system 205 may be received by the egress port of node A 220. Once received, the data packet may be transmitted or sent to one or more packet processing units, such as an egress PPU ("EPPU") 1 430, which may perform one or more processes on the received data packets before passing them to an egress traffic manager ("ETM") 435. For example, the EPPU1 430 may perform destination multicast resolution to determine all of the destination egress ports.

The ETM 435 may be a memory, buffer, or storage which may receive data packets, or data segments, from the egress port. The ETM 435 may store the received data packets or data segments until the egress port of the node A 220 is ready to send or transmit the data packet to a device in connection with the node A 220 (such as the server 110). In some systems, the egress port of the node A 220 may not be ready to send or transmit data packet to a device in connection with the node A 220 until the entire data packet has been received at the egress port of node A 220. In some systems, the egress port of the node A 220 may not be ready to send or transmit data packet to the device in connection with the node A 220 until the device indicates that it is ready to receive the data packet. In some systems, the egress port of the node A 220 may not be ready to send the data packet stored in the ETM 435 until one or more combinations of these or other conditions are satisfied. Other variations are possible.

When the egress port of node A 220 is ready to send the data packet to the device, the data packet may be sent from the ETM 435 one or more packet processing units, such as an EPPU2 440, which may perform some processing on the data packets prior to transmitting the data packets from the egress port. Afterwards, the data may be transmitted to the device, such as by or through an interface. In other examples, the data packet may be sent from the ETM 435 directly to the device, without any further processing of the data packet.

In some systems, a node or tile, such as node A 220, may additionally or alternatively include one or more controllers or control modules. A port of a node or tile may have a controller or control modules. Controllers, control components, or control modules may include one or more of the components of the node A 220, or various other components. The controllers or control modules may perform various functions or tasks. For example, the control modules may analyze and determine a destination egress port from a received data segment or data packet. As another example, a control module may perform one or functions, run one or more algorithms, and/or make one or more determinations which may affect or control a function or performance of the node or a port of the node. The controllers or control modules may perform various other functions or tasks.

In contrast to the store-and-forward data transfer, in some systems, data packets may be processed and transmitted from an ingress port of node A 220 using a cut-through data transfer (sometimes referred to as "cut-through," "cut-through switching," or "cut-through data transfer"). With cut-through, partial data frames or packets can be forwarded before the whole frame has been received, such as soon as the destination address is processed. With cut-through, data segments of a data packet may be transferred by an ingress port or ingress node to an egress port or egress node without being stored in a buffer or memory of the ingress node, such as the ITM 415.

In cut-through, data segments or a data packet may be received by the node A 220. In cut-through, however, the data segments or a data packet may gain access to the fabric bandwidth after an initial packet processing at the IPPU1 410 to determine a destination node, without waiting for the full data packet to have arrived at the ingress node. For example, the received data segments may be sent by the ingress port of the node A 220 to the egress port of the recipient node immediately upon receipt and resolution of the destination node, without waiting for all data segments of the data packet to be received. The data segment of a data packet may be transmitted by the ingress port of node A 220 to the recipient node before all of the other data segments of the data packet have been received at or processed by the ingress port of node A 220.

The received data segments may, in some instances, be transmitted to the egress port without being stored in any physical memory or a buffer, such as ITM 415. Alternatively, the one or more data segments may be stored in memory prior to transmission to the egress port. Because the data segments transmitted using cut-through may bypass physical memory or a buffer, no time may be needed or spent reading data out from the memory or buffer. Additionally, cut-through data transfers may create a lower delay, as some data segments may be transferred prior to receipt of the entire data packet. As such, cut-through data transfers may lower delays and/or be faster and more-efficient than store-and-forward data transfers for transferring data packets between ingress ports and egress ports.

Ingress ports or nodes and egress ports or nodes may be referred to as operating in a "store-and-forward mode" or in a "cut-through mode." When operating in store-and-forward, the ingress ports may transmit data to a destination egress port using a store-and-forward data transfer, and the egress ports may receive data from an ingress port using a store-and-forward data transfer. When operating in cut-through, the ingress ports may transmit data to a destination egress port using a cut-through data transfer, and the egress ports may receive data from an ingress port using a cut-through data transfer. Other terms and variations are possible.

In some instances, however, it may not be possible to transfer data or data packets to an egress port using a cut-through data transfer. For example, cut-through may require that no other ingress port is using or plans to send data or a data packet to the same egress port. As such, it may not be possible to transfer data segments or a data packet to an egress port using a cut-through data transfer where more than one ingress port have data destined to be transmitted to the same egress port at the same time. For example, data 300 may be received by the ingress port of ingress node A 310 at the same time that data 303 may be received by an ingress port of ingress node D 313, and both the data 300 and the data 303 may be intended or destined for an egress port of egress node C 422. The egress port of egress node C 322 may not be capable of receiving cut-through data from both the ingress port of ingress node A 310 and the ingress port of ingress node D 313 at the same time. Performing data transfer using cut-through under such circumstances may lead to collisions between data being sent to the egress port, and may result in data delay or data loss.

Ingress nodes may determine a state of an egress node and whether or not cut-through data transfer is possible by identifying and analyzing ingress and egress cut-through statement vectors. Ingress nodes or ingress ports may generate, create, determine, and/or otherwise use ingress cut-through statement vectors. The ingress cut-through statement vector may be a mathematical vector which may indicate whether the ingress node or ingress port generating the ingress cut-through statement vector has any data to be transmitted or otherwise sent to an egress port. The control modules of the port or node may generate the cut-through statement vectors for the ports or nodes.

Ports or nodes may generate, create, determine, and/or otherwise use cut-through statement vectors to determine whether to use a cut-through data transfer or another data transfer type, such as a store-and-forward data transfer. Ingress nodes that receive and/or identify ingress cut-through statement vectors from other ingress nodes in the system may determine whether or not the other ingress nodes have any data to be sent or transmitted to an egress node or port.

Cut-through statement vectors may be generated, created, updated, and/or otherwise used every clock cycle, periodically, at various time intervals, when triggered (such as every time data is received by a port or node of a system or every time a data packet transmission is completed), or at various other times. Using cut-through statement vectors effectively may allow for a collision-free cut-through decision to be made by the ingress port or ingress node independently.

One or more components of a port or node, such as a control module of a port, or nodes may create, generate, and use a cut-through statement vector for one or more ingress ports or ingress nodes and one or more egress ports or egress nodes of a system 105. A cut-through statement vector may be created, for example, for ingress ports in a system 105, or for ingress nodes in a system 105, and may be referred to as an ingress cut-through statement vector or an ingress node statement. Where the ingress port creates or has an ingress cut-through statement, the ingress cut-through statement may include an entry for the egress ports of the system 105. An entry of the ingress cut-through statement vector may indicate whether or not the ingress port that the ingress cut-through statement was created for has pending data for or to be transmitted to the associated egress port. Where ingress nodes create or have ingress cut-through statements, the ingress cut-through statement vector may include multiple columns (or rows), with columns being associated with one ingress port of the ingress node and including entries for egress ports of the system to indicate whether the ingress port associated with the column (or row) has data for the egress port associated with the entries. In some systems, an ingress port statement may refer to an ingress cut-through statement vector generated, created, and used by or for an ingress port. In some systems, an ingress port statement may refer to set of entries, such as a column (or row), of an ingress cut-through statement vector for an ingress node that corresponds to the ingress port. Other variations are possible.

In some systems, an ingress cut-through statement vector includes entries for every egress port of a system. Ingress cut-through statement vectors may only include entries and/or values for some egress ports, such as those egress ports which are not disabled, or those egress ports may be configured or capable of receiving data from the ingress port. Other variations are possible.

In some systems, an ingress cut-through statement vector may include entries or bits for different class of services or priority levels. For example, an ingress cut-through statement vector with one class of service or priority level may include one value for an egress port. As another example, an ingress cut-through statement vector for an ingress node with four class of services or priority levels may include four values for an egress port, the four values corresponding to the four class of services. An ingress cut-through statement vector may include columns for class of service or priority levels and rows for the egress ports or egress nodes. Other variations are possible.

Figure 5:
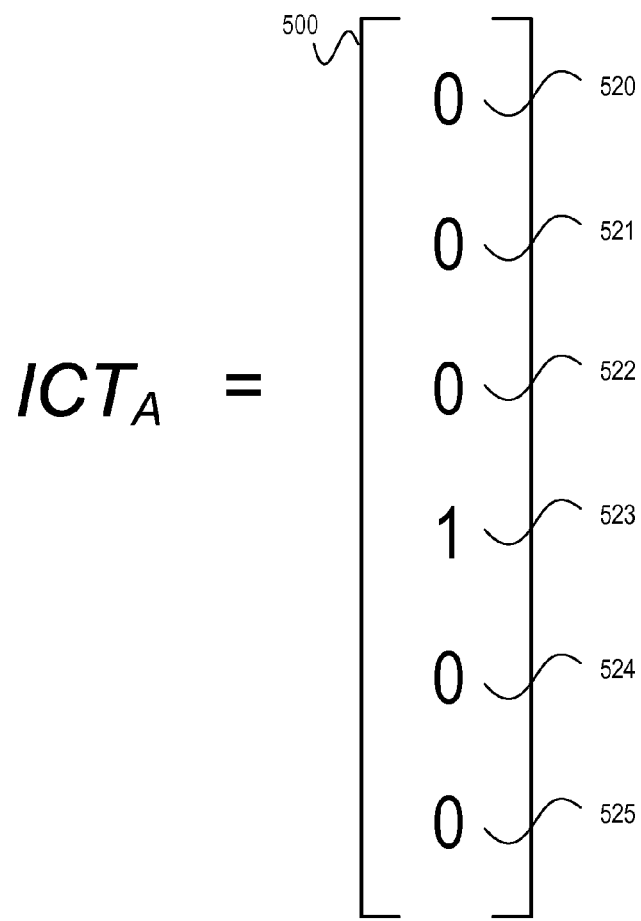
FIG. 5 is a diagram of an exemplary ingress cut-through statement vector.

FIG. 5 is a diagram of an exemplary ingress cut-through statement vector 500. The ingress cut-through statement vector 500 (denoted as "$ICT_A$") may be an ingress cut-through statement vector for an ingress port of the system 305 shown in FIG. 3, such as an ingress port of the ingress node A 310.

The ingress cut-through statement vector 500 for the ingress port of ingress node A 310 may include an entry for the six egress ports of the egress nodes 320-325 of that system 305. For example, entry 520 may correspond to the egress port of the egress node A 320, entry 521 may correspond to the egress port of the egress node B 321, entry 522 may correspond to the egress port of the egress node C 322, entry 523 may correspond to the egress port of the egress node D 323, entry 524 may correspond to the egress port of the egress node E 324, and entry 525 may correspond to the egress port of the egress node F 325. In some systems, the ingress cut-through statement vector may have a vector size equal to the number of ingress ports.

The control module or an ingress node or port may set or include a value for entries of the cut-through statement vector 500. The value of the entry may indicate whether or not the ingress port has data that may be present for the egress port associated with the entry. Entries may be one of two values, indicating whether or not data is present at that ingress port for the egress port associated with the entry. Entries may either be a "0" (indicating no data present at the ingress port for the egress port associated with the entry) or a "1" (indicating data present at the ingress port for the egress port associated with the entry). While values of "0" and "1" are shown, these may be replaced with "low" and "high" indicators or various other indicators which may show two different states. In addition or alternatively, entries may have or be one of three or more values, associated with one or more other states of the ingress port.

One, some, or all of the other ingress port of the system 305 in FIG. 3 may also generate or create an ingress cut-through statement vector. Ingress cut-through statement vectors for the ingress ports of the system 305 may indicate whether or not the ingress port have data which is available for transmission to the egress ports of the system 305

A control module for an ingress port or ingress node may create an ingress cut-through statement vector for the ingress port or ingress node. An ingress cut-through statement may be created for an ingress node, regardless of the number of ingress ports included with the ingress node. Alternatively, an ingress cut-through statement vector may include separate information for the ingress ports of the ingress nodes.

Figure 6:
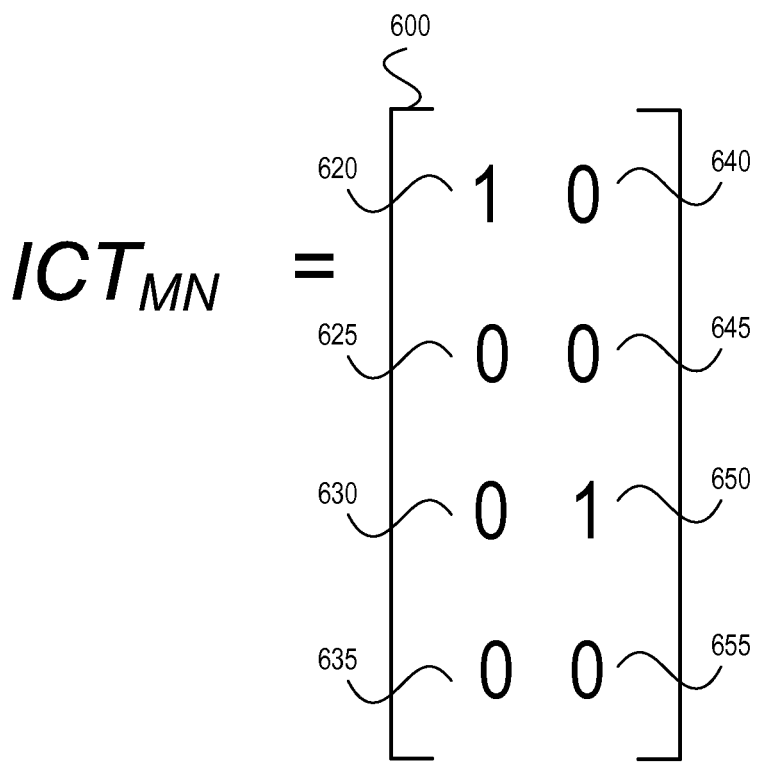

FIG. 6 is a diagram of an exemplary ingress cut-through statement vector 600 (denoted as "$ICT_{MN}$") with information for more than one ingress port of an ingress node. The ingress cut-through statement vector 600 may be an ingress cut-through statement vector for an ingress node that may have two ingress ports. The ingress cut-through statement vector 600 may include a set of entries, such as entries in a column (or row), for ingress ports. For example, cut-through statement vector 600 may include a first column, such as the left hand column of the cut-through statement vector 600, which may be associated with a first ingress port, and a second column, such as a right hand column of the cut-through statement vector 600, which may be associated with the second ingress port of the ingress node.

Entries of the ingress cut-through statement vector 600 for an ingress port may include an entry for each of the egress ports of that system 205. Entry 620 may be the entry associated with the first ingress port of the ingress node for a first egress port of the system, and entry 640 may be the entry associated with the second ingress port of the ingress node for the same first egress port of the system. Entry 625 may be the entry associated with the first ingress port of the ingress node for a second egress port of the system, and entry 645 may be the entry associated with the second ingress port of the ingress node for the same second egress port of the system. Entry 630 may be the entry associated with the first ingress port of the ingress node for a third egress port of the system, and entry 650 may be the entry associated with the second ingress port of the ingress node for the same third egress port of the system. Entry 635 may be the entry associated with the first ingress port of the ingress node for a fourth egress port of the system, and entry 655 may be the entry associated with the second ingress port of the ingress node for the same fourth egress port of the system.

The high or "1" value for the entry 620 of the cut-through statement vector 600 may indicate that the first ingress port of the ingress node may have data present to be transmitted or sent to the egress port associated with the entry 620 (such as the first egress port of the system). The low or "0" values for the other entries 625, 630, and 635 may indicate that the first ingress port of the ingress node may not have data present to be transmitted or sent to the second, third, or fourth egress ports of the system. The high or "1" value for the entry 650 of the cut-through statement vector 600 may indicate that the second ingress port of the ingress node may have data present to be transmitted or sent to the third egress port of the system, while the low or "0" values for the other entries 640, 645, and 655 may indicate that the second ingress port of the ingress node may not have data present to be transmitted or sent to the first, second, or fourth egress ports of the system. Ingress cut-through statement vector 600 may be useful for an ingress node itself, such as to determine which of its ingress ports should be given a priority of data transfer. Various other examples and configurations of ingress cut-through statement vectors 500 and 600 are possible.

In some instances, an entry of the ingress cut-through statement vectors, such as ingress cut-through statement vectors 500 and 600, may indicate or have a high value if the ingress port has store-and-forward data for an egress port associated with the entry. For example, an ingress cut-through statement vector may provide an indication that the ingress port has store-and-forward data for an egress port that resides in a component of a node, such as the ITM 415 or fabric of a system 305.

In determining whether or not store-and-forward data resides in an ingress port of a node, various data or counts may be analyzed or considered. As a first example of a count that may be used to determine if data is in the ITM 415, the determination may be based on or require a count of store-and-forward cells stored in the ITM 415, which may be referred to as an ITM_SAF_COUNT[i]. This count may be incremented when data arrives at the ingress port, and may be decremented when data is transmitted from the ITM 415. As an example of a timer that may be used, the determination may be based on or require a countdown timer that may be used to account for data or data packets that may be delayed because of one or more events, such as a departure from the ITM 415 or a reception at an inter-tile receive ("ITR") component. The ITR component may receive data from one or all of the ingress nodes, and/or may act as a receiver at the egress node. This timer may be referred to as a LISTENER_DELAY_TIMER[i] and may indicate when ingress ports have or do not have data for the egress port. The egress port may be considered "empty" or have no data present when the ITM_SAF_COUNT has a count or value equal to zero, and when the LISTENER_DELAY_TIMER has expired. Other counters or examples may implemented or used with this system.

Egress nodes or egress ports may generate, create, determine, and/or otherwise use egress cut-through statement vectors. The egress cut-through statement vector may be a mathematical vector which may indicate whether the egress node or egress port generating the egress cut-through statement vector is idle, available, or otherwise operable to receive data from an ingress node or ingress port through a cut-through data transfer. The control modules of the port or node may generate the cut-through statement vectors for the ports or nodes.

Ports or nodes may generate, create, determine, and/or otherwise use egress cut-through statement vectors to determine whether to use a cut-through data transfer or data transfer type, such as a store-and-forward data transfer. Ingress nodes that receive and/or identify egress cut-through statement vectors from egress nodes or egress ports may determine whether or not the egress nodes or ports are idle, available, or otherwise operable to receive data from an ingress node.

Egress cut-through statement vectors may include one or more entries which may indicate whether an egress port associated with the entry is idle or capable and available to receive data from an ingress port using cut-through. Where an egress cut-through statement is created for egress nodes, the egress cut-through statement vector may include multiple entries, with entries being associated with one egress port of the egress node and including a value for the egress ports of the system to indicate whether the egress port associated with the entry is capable and available to receive data from an ingress port using cut-through. Where an egress cut-through statement is created for egress ports, the egress cut-through statement may include only one entry for the egress port of the system 105, indicating whether or not the egress port is idle or capable and available to receive data from an ingress port using cut-through. Other variations are possible.

A cut-through statement vector generated, created, and used by or for an egress port or egress node may be referred to as an egress cut-through statement vector, an egress port statement, or an egress node statement. In some systems, an egress port statement may refer to an egress cut-through statement vector created for the egress port. In other systems, an egress port statement may refer to an entry corresponding to the egress port of an egress cut-through statement vector for an egress node that includes the egress port.

Figure 7:
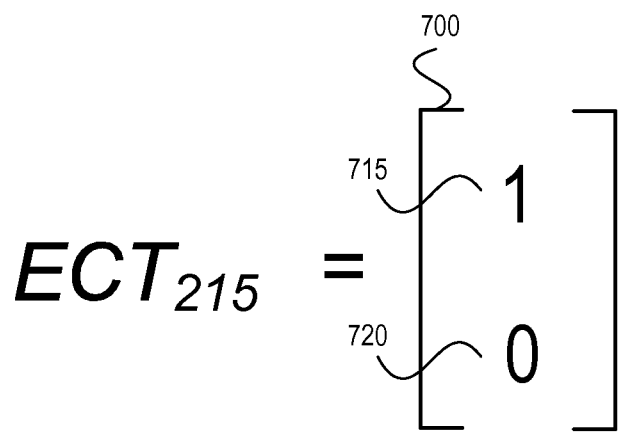
FIG. 7 is a diagram of an exemplary egress cut-through statement vector.

In some systems, an egress cut-through statement vector may include entries or bits for different class of services or priority levels. For example, an egress cut-through statement vector with one class of service or priority level may include one value for each egress port. As another example, an egress cut-through statement vector for an egress node with four class of services or priority levels may include four values for each egress port, the four values corresponding to the four class of services. The values may indicate whether or not the egress port associated with the value is flow controlled or able to accept data for data associated with the corresponding class of service. Egress cut-through statement vectors may, for example, include columns for the class of services or priority levels, and rows corresponding to the egress ports. Other variations are possible FIG. 7 is a diagram of an example egress cut-through statement vector 700 (denoted as "$ECT_{220}$"). An egress cut-through statement vector 700 may be created, generated by, and/or sent for dies in a system. In some systems, the size of the cut-through statement vector 700 may correspond to the number of egress ports included in egress nodes, and an entry of the cut-through statement vector 700 may correspond to one of the egress ports. An egress cut-through statement vector may be referred to as an egress port statement, or an egress node statement For example, egress cut-through statement vector 700 may be associated with or generated or created for an egress node having two egress ports. The cut-through statement vector 700 may have two entries 715 and 720. Entry 715 may be associated with a first egress port of the egress node, while entry 720 may be associated with a second egress port of the egress node.

A separate egress cut-through statement vector 700 may be created, generated, and/or sent for egress ports in a system, regardless of the number of ports per node. Egress cut-through statement vectors may only have one entry, which may correspond to the state of the egress port itself. Other variations are possible.

Entries in the egress cut-through statement vector 700 may indicate whether or not the egress port may receive cut-through data from any of the ingress ports of the system. A value of "0" or "low" value may indicate the egress port is capable or configured to receive cut-through data from an ingress port, while a value of "1" or "high" may indicate that the egress port is not capable or configured to receive cut-through data. In other systems, the values may be reversed. In still other systems, more values or different entries may be possible, and may indicate various other states.

Various states, functions, and circumstances may cause a value of an entry in the egress cut-through statement vector 700 to indicate that the egress port is not capable or able to receive cut-through data. For example, an entry of the egress cut-through statement vector 700 may indicate that the associated egress port is not capable or able to receive cut-through data when the egress port already has data which it received or data which it is internally processing. As an example, an egress cut-through statement may provide an indication that store-and-forward data resides in one or more blocks of a node for a given egress port. In some systems, an egress port may still be eligible for cut-through even when data exists or is needed at the egress port, such as when the egress port needs data for a packet or is finishing transmitting a prior packet. Other variations are possible.

In determining whether or not data resides in an egress port of a tile or node, various data or counts may be analyzed or considered. As a first example of a count that may be used to determine if data is in the ITR component, the determination may be based on or require a count of store-and-forward cells stored in the ITR component, which may be referred to as an ITR_SAF_COUNT[i]. This count may be incremented when data arrives at the egress port from an ingress port, and decremented when data is transferred the EPPU1 430. As an example of a count that may be used to determine if data is in the ETM 435, the determination may be based on or require a count of store-and-forward cells stored in the ETM 435, which may be referred to as an ETM_SAF_COUNT[i]. This count may be incremented when data arrives at the ETM 435, and may be decremented when the data is transmitted from the ETM 435. As an example of a timer that may be used to determine if data is in the EPPU2 440, the determination may be based on or require a countdown timer that may be used to account for packets being processed in the EPPU2 440, which may be referred to as an EPPU2_SAF_DELAY[i]. This counter may be started when an ITR_SAF_COUNT transitions to zero ("0") for an egress port. The egress port may be considered "empty" or have no data present in the egress port when both of the ITR_SAF_COUNT and the ETM_SAF_COUNT have counts or values equal to zero, and when the EPPU2_SAF_DELAY delay timer has expired. Other counters or examples may be possible.

Additionally or alternatively, an entry of the egress cut-through statement vector 700 may indicate that the associated egress port is not capable or able to receive cut-through data when the egress port is flow controlled or otherwise instructed not to receive further data. As another example, the value of an entry of the egress cut-through statement vector 700 may indicate that the associated egress port cannot receive data using cut-through when the egress port is not functioning properly or is otherwise disabled. Various other examples are possible.

Where no states, functions, or circumstances are occupying the egress port, such as where there is no data for the egress port and where the egress port is not flow controlled, the value of an entry of the egress cut-through statement vector 700 associated with the egress port may indicate that the egress port is capable or operable to receive data from an ingress port via a cut-through data transfer. Various other examples or variations of egress cut-through statement vectors are possible.

A control module for ingress ports or nodes and egress ports or nodes may create, generate, and use the cut-through statement vectors. For example, the control module may transmit the created ingress and egress cut-through statement vectors to one or more ports or nodes of a system. Nodes or ports in a system may use the information in the cut-through statement vectors to make determinations about whether or not to perform data transfer using a cut-through data transfer another data transfer type, such as store-and-forward. In some systems, control modules of ingress nodes may perform some or all determinations, algorithms and functions to determine whether any of the ingress ports of the ingress node may transmit data to an egress port using cut-through. In other systems, control modules ingress ports may perform some or all determinations, algorithms and functions to determine whether the ingress ports may transmit data to an egress port using cut-through. Other variations are possible.

Figure 8:
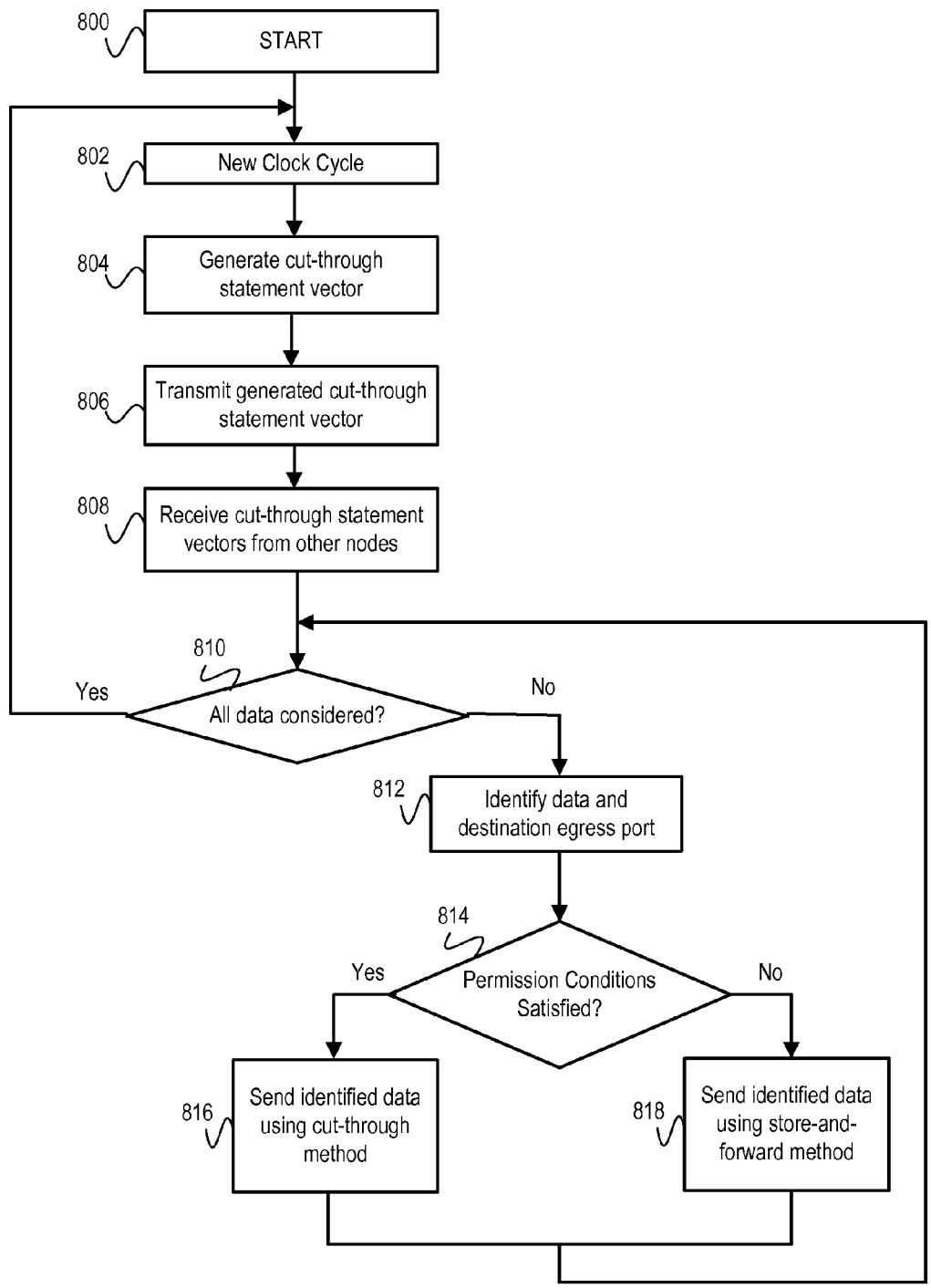
FIG. 8 is a flow diagram of an exemplary logic for transferring data.

FIG. 8 is a flow diagram of an exemplary logic for transferring data. The logic may include determining, at an ingress node or ingress port, whether an ingress port may transfer a data or data packet to a destination egress port using a cut-through data transfer. The logic of FIG. 8 may be performed, for example, by a controller or control module of any of the ingress nodes or ingress ports of a system, such as by a control module of ingress node A 310 of the system 305. While the logic may be described with reference to an ingress port of ingress node A 310, it should be appreciated that any of the ingress ports or ingress nodes of any of the systems 105, 205, or 305 may incorporate or perform one or more functions of this logic.

At block 800, the logic may begin. At block 802, a new clock cycle may begin. The logic may be performed each clock cycle. Alternatively or additionally, the logic may be performed according to other factors, such as when a new packet is received for a given egress port, when it is determined that a data packet has been fully transmitted to the egress port, or at various other times.

At block 804, the a control module of the ingress node A 310 (or an ingress port) may create, generate, or otherwise prepare an ingress cut-through statement vector, such as an ingress cut-through statement vector 500 or 600. The ingress cut-through statement vector may be similar to or resemble the ingress cut-through statement vector 500, and/or may be created for ingress ports of the system. Additionally or alternatively, the ingress cut-through statement vector may be similar to or resemble the ingress cut-through statement vector 600, and/or may be created for ingress nodes. Other variations are possible.

The ingress cut-through statement vector may include entries for the egress ports of the system. The ingress cut-through statement vector may include a value for the entries, which may indicate whether or not the ingress port may have data present to be sent to the egress port.

At block 806, the ingress node, or a control module of the ingress node, may send or transmit the generated ingress cut-through statement vector to one or more of the other ingress nodes, or ingress ports. For example, in some systems, the ingress node A 310 sends the ingress cut-through statement vector to all ingress nodes of the system 305, including to ingress node B 311, ingress node C 312, ingress node D 313, ingress node E 314, and ingress node F 315. In this way, all of the ingress nodes 310-315 in the system 305 may receive, gather, identify, determine, and/or include information regarding which egress port that the ingress ports of the ingress node A 310 may have data to be transmitted to. In some of these systems, the ingress node (or control module of the ingress node) may not send the ingress cut-through statements to any of the egress port, as the decisions regarding whether to send data using cut-through or another data transfer type may be made by the ingress nodes.

At block 808, the ingress node, or ingress ports, may receive cut-through statement vectors from one or more other nodes or ports of the system 305. For example, the ingress node A 310 may receive ingress cut-through statement vectors from the other ingress nodes 311-315 of the system. In this example, the ingress ports or ingress nodes 310-315 in the system 305 may receive, gather, identify, determine and/or include information regarding which egress ports that all of the other ingress ports or ingress nodes 310-315 of the system 305 may have data to be transmitted to.

Additionally or alternatively, the ingress node may receive one or more egress cut-through statement vectors from one or more egress nodes or egress ports of the system 305. For example, the ingress node A 310 may receive an egress cut-through statement vector from all of the egress ports or egress nodes in the system 305, including the egress node A 320, egress node B 321, egress node C 322, egress node D 323, egress node E 324, and egress node F 325. In this example, the ingress node A 310 may be aware of whether or not the egress ports of the egress nodes 320-325 of the system 305 may be capable or otherwise operable to receive cut-through data from any of the ingress ports.

The ingress port may have data or one or more data packets that may be present to be transmitted or sent to one or more of the egress ports of the egress nodes 320-325 of the system. At block 810, the ingress node having the ingress port, or the ingress port itself, may determine whether or not all of the data or data packets have been considered or analyzed in light of the receiving ingress and egress cut-through statement vectors. Where the ingress port has no data present to be transmitted to one or more of the egress ports of the egress nodes 320-325, the logic may return to block 802 and await the next clock cycle or point in time when a new set of cut-through statement vectors are to be generated and distributed to and between the ingress and egress nodes.

Where the ingress port has at least one set of data or data packet to be transmitted or sent to one or more of the egress ports of the egress nodes 320-325, the logic may proceed to block 812. At block 812, a set of data or data packet may be identified. Additionally, the destination egress port for the identified set of data or data packet may be identified or otherwise determined.

At block 814, a control module of the ingress node or the ingress port may analyze the received cut-through statement vectors to determine whether one or more permission conditions are satisfied allowing for the data to be transmitted to the egress port using cut-through, or whether a conflict may exist for the identified data or data packet.

As an example, one permission condition that an ingress port may need to satisfy to transfer data to a destination egress port via cut-through may be to ensure that no other ingress port have data to be sent to the same egress port. In verifying this permission condition, the ingress node including the ingress port, or the ingress port itself, may analyze or otherwise determine from all of the received ingress cut-through statements from the other ingress nodes 311-315 whether or not any of the other ingress ports of the ingress nodes 311-315 also have data to be transferred or delivered to the destination egress port. In performing this analysis, the ingress node may identify entries in the ingress cut-through statement vectors from the other ingress ports that corresponds to the destination egress port. If an entry in any of these ingress cut-through statement vectors associated with the destination egress port indicates that one of the associated ingress ports of the ingress nodes 311-315 has data to be transmitted to the destination egress port, a conflict may arise. In this circumstance, the permission condition may not be satisfied, and the ingress port may not send the data to the destination egress port via the cut-through data transfer. If instead no entries of the ingress cut-through statement vectors associated with the destination egress port indicates that one of the associated ingress ports of the ingress nodes 311-315 has data to be transmitted to the destination egress port, this permission condition may be satisfied.

As another example of a permission condition that the ingress port may need to satisfy before sending data to the destination egress port via cut-through, the ingress node having the ingress port, or the ingress port itself, may need to verify that the egress port is idle or capable and available to receive the data from the ingress port using cut-through. For example, the ingress node may need to verify that the egress port is idle and not busy. The ingress node may need to verify that the egress port does not have any data already in the egress port, and that the egress port is not flow controlled. The ingress node may identify and analyze the egress cut-through statement vector which may be associated with or include an entry for the destination egress port. If the entry for the egress port indicates that the egress port is not capable or available to receive any cut-through data, a conflict may arise and the permission condition may not be satisfied. In these circumstances, the ingress port may not send the data to the destination egress port via a cut-through data transfer. If instead the entry for the egress port indicates that the egress port is capable or available to receive any cut-through data, this permission condition may be satisfied.

As another example of a permission condition, the ingress node including the ingress port, or the ingress port itself, may need to confirm that the local ingress node does not have any data in a store-and-forward path for the destination egress port. As another example, in some systems, the ingress port and the egress port may be required to operate or transmit data at the same speed in order for the ingress port to provide data to the egress port using cut-through. Various other permission conditions may exist which an ingress port may need to satisfy before proceeding with transferring data to a destination egress port using cut-through.

In some systems, a plurality of permission conditions must be satisfied before the ingress node may be authorized to transfer or deliver the data by the ingress port to the destination egress port via cut-through. For example, in some systems, the ingress port must verify that no other ingress port have data for the egress port, that the egress port is capable and available to receive data using cut-through (or is otherwise idle), and that the ingress port does not have any stored data to be transmitted to the egress port in a store-and-forward data transfer. In other systems, only one, some, or different permission conditions may need to be satisfied.

If the control module or other component of the ingress node determines that the permission conditions are satisfied and no conflict arises from the analysis of the egress cut-through statement of the destination egress port, the logic may proceed to block 816. At block 816, the ingress port may proceed to send the data or data packet it has to the destination egress port as cut-through data or as data sent or transferred using cut-through.

If instead the permission conditions are not satisfied, the ingress port may not be able, operable, configured, or allowed to send the data to the destination egress port using cut-through. In these circumstances, the logic may proceed to block 818, where the ingress port may proceed to send the identified data to the egress port using a different data transfer type, such as using a store-and-forward data transfer.

After either block 816 or 818, the logic may proceed back to block 810. At block 810, the ingress node or ingress port may determine if another set of data or data packet resides at the ingress port that it has which is to be sent to or transmitted to an egress port. If another set of data or data packet exists at the ingress port and has not been previously identified in block 812, the ingress node or ingress port may select that set of data or data packet and proceed to block 812. If all of the sets of data or data packets have already been identified and considered in blocks 812, the logic may return to block 802 and await the next clock cycle or trigger event. Other variations may exist.

In some variations, the logic of FIG. 8 may include fewer or more blocks or functions. In some systems, one or more blocks may perform different functions. For example, block 802 may not be triggered at a new clock cycle, but rather may be triggered anytime a trigger event occurs, such as when a new set or data or data packet arrives at one of the ingress nodes, when transmission of a data packet to an egress port via store-and-forward or cut-through ends or finishes, when transmission of a segment or portion of a data packet to an egress port ends or finishes, when an egress port indicates that it is idle or otherwise available to receive data via a store-and-forward or a cut-through data transfer, when a state or status of an ingress or egress port changes, or at various other times.

In some systems, one or more blocks or functions may be performed in a different order or at the same time. For example, blocks 806 and 808 may be performed simultaneously or in a different order. One or more blocks may be combined into fewer functions or determinations. For example, blocks 810 and 812 may be combined into one block. Various other examples and variations are possible.

In some systems, all of the ingress nodes of the system may execute logic like the logic in FIG. 8 simultaneously and independently. As all of the ingress nodes may have the same information and may run the same algorithms or functions to determine whether the ingress ports are able to perform cut-through data transfers, ingress nodes may determine an outcome for the system. As such, there may be no need for any additional communications between the ingress nodes indicating which nodes will proceed to perform cut-through data transfers based on the cut-through statement vectors. This may streamline, simplify, and expedite decisions about performing cut-through data transfers, and may avoid a centralized system for controlling cut-through determinations.

Figure 9:
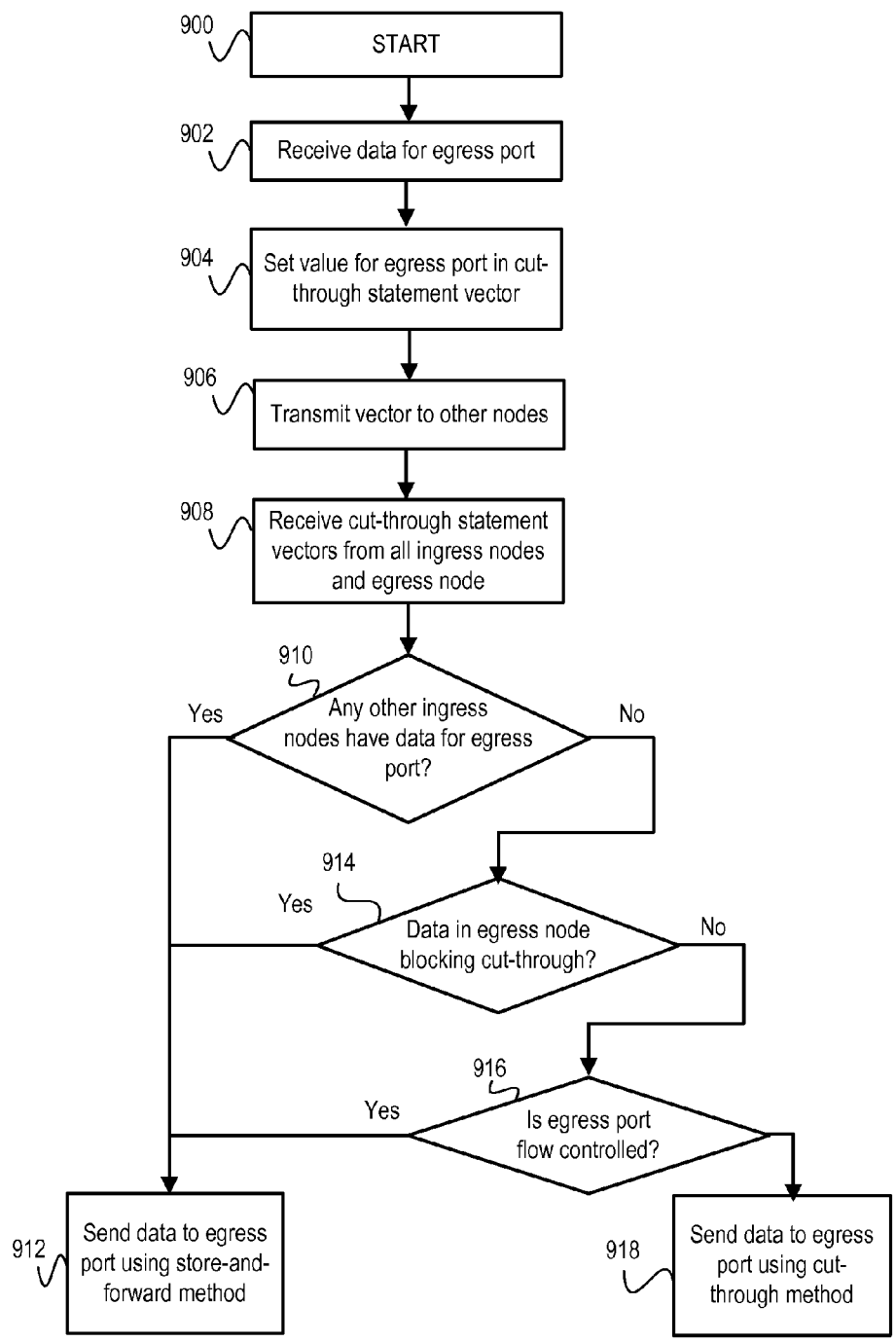
FIG. 9 is a flow diagram of an exemplary logic for transferring data.

FIG. 9 is a flow diagram of an exemplary logic for transferring data from an ingress port to a destination egress port. The logic of FIG. 9 may, for example be carried out or performed by one or more controllers or control modules of one or more ingress nodes or egress nodes. The logic of FIG. 9 may begin at block 900.

At block 902, data, or a data packet, may be received at an ingress port of an ingress node. The data may be intended for or destined to be delivered to an egress port. One or more components of the ingress node, such as an IPPU1 410, may determine the destination egress port from the data or information about the data.

At block 904, the ingress node may set a value for an entry associated with the egress port in a cut-through statement vector for the ingress node. For example, the ingress node may change or set the value of the entry of the cut-through statement vector associated with the egress port to a "1" or "high" value which may indicate that the ingress node has data for the egress port. In some systems, entries of a cut-through statement vector may default to a value (such as "0") that indicates that the ingress node does not have any data for the egress port associated with the entry. In some of these systems, the ingress node at block 904 may change or set the value of the entry of the cut-through statement vector to a different value (such as "1") that indicates that the ingress node now does have data for the egress port associated with the entry.

The ingress node may repeat blocks 902 and/or 904 for each piece of data that is received at an ingress port of the ingress node. For example, if the ingress port receives data for two egress ports, such as for an egress port in the egress node C 322 and an egress port in the egress node F 325, the receiving ingress node may set the value in the ingress cut-through statement vector for the entries associated with both of the egress ports in egress nodes 322 and 325 before proceeding to block 906. Other variations are possible.

At block 906, the ingress node may transmit or transfer the cut-through statement vector to one or more other nodes. The ingress node may, for example, transmit or transfer the cut-through statement vector to all of the other ingress nodes of the system. The function and operation of block 906 may be similar to or resemble the function and operation of block 806 of the logic of FIG. 8.

At block 908, the ingress node may receive ingress cut-through statement vectors from all of the other ingress nodes in the system, as well as an egress cut-through statement vector from the destination egress port or the egress node including the destination egress port. In some systems, such as systems where blocks 902 and/or 904 were repeated for multiple egress ports, the ingress node may receive egress cut-through statements from the destination egress ports. The function and operation of block 908 may be similar to or resemble the function and operation of block 808 of the logic of FIG. 8.

At block 910, the ingress node may determine whether any other ingress nodes have data that is destined for or intended to be sent or delivered to the destination egress port. For example, the ingress node may identify entries in the ingress cut-through statement vectors from the other ingress nodes that corresponds to the destination egress port.

If an entry in any of these ingress cut-through statement vectors associated with the destination egress port indicates that one of the associated ingress nodes has data to be transmitted to the destination egress port, the logic may proceed to block 912. At block 912, the data at the ingress node may be sent to the egress port using a store-and-forward data transfer.

If instead none of the ingress cut-through statement vectors indicates that one of the associated ingress nodes has data to be transmitted to the destination egress port, the logic may proceed to block 914. At block 914, the ingress node may determine whether or not data is present in the egress node which may block cut-through to the egress port. This determination may be made by analyzing or reviewing the egress cut-through statement vectors to determine whether or not the egress port has data present that may block cut-through to the egress port. Additionally or alternatively, the egress cut-through statement vector may have a value that indicates that the egress port has data present that may block cut-through to the egress port. Additionally or alternatively, the egress cut-through statement may have a value that indicates merely that the egress port cannot accept any cut-through data. Additionally or alternatively, the egress port may be queried or send other information regarding whether or not data is present at the egress port. Other variations are possible.

If the egress port has data present in it, the logic may proceed to block 912. At block 912, the data at the ingress port may be sent to the egress port using a store-and-forward data transfer.

If the egress port does not have data present, the logic may proceed to block 916. At block 916, the ingress node may determine whether or not the egress port is flow controlled or not. Additionally or alternatively, this determination may be made by analyzing or reviewing the egress cut-through statement vectors to determine whether or not the egress port is flow controlled. Additionally or alternatively, the egress cut-through statement vector may have a value that indicates that the egress port is flow controlled. Additionally or alternatively, the egress cut-through statement may have a value that indicates merely that the egress port cannot accept any cut-through data. Additionally or alternatively, the egress port may be queried or send other information regarding whether or not the egress port is flow controlled.

The determination at block 916 may be made depending on a class of service or priority level associated with the data to be sent to the egress port. The data received at block 902 may be associated with one of a number of class of services. The destination egress port may be flow controlled for some class of services and not for others. At block 916, the system may determine whether the egress port is flow controlled for the class of service of the data received at block 902. The system may, for example, use an egress cut-through statement vector that includes values for each egress port and class of service to make the determination, such as an egress cut-through statement vector that contains a bit per egress port-class of service pair. Other variations are possible.

If the egress port is flow controlled, the logic may proceed to block 912. At block 912, the data at the ingress port may be sent to the egress port using a store-and-forward data transfer.

If the egress port is not flow controlled, the logic may proceed to block 918. At block 918, the data may be sent or transmitted to the egress port using the cut-through data transfer.

In some variations, the logic of FIG. 9 may include fewer or more blocks or functions. For example, where additional or different permission conditions exist other than those in blocks 910, 914, and 916, these additional or different permission conditions may be included in the logic. In some implementations, one or more blocks may perform different functions. In some implementations, one or more blocks may be combined into fewer functions or determinations. Additionally or alternatively, one or more blocks or functions may be performed in a different order or at the same time. For example, blocks 910, 914, and 916 may be performed simultaneously or in a different order. Various other examples and variations are possible.

In some systems, all of the ingress nodes (or all of the ingress ports) of the system may execute logic like the logic in FIG. 9 simultaneously and independently. As all of the ingress nodes may have the same information and may run the same algorithms or functions to determine whether they are able to perform cut-through data transfers, ingress nodes may determine an outcome for the system. As such, there may be no need for any additional communications between the ingress nodes indicating which nodes will proceed to perform cut-through data transfers based on the cut-through statement vectors. This may streamline, simplify, and expedite decisions about performing cut-through data transfers.

Figure 10:
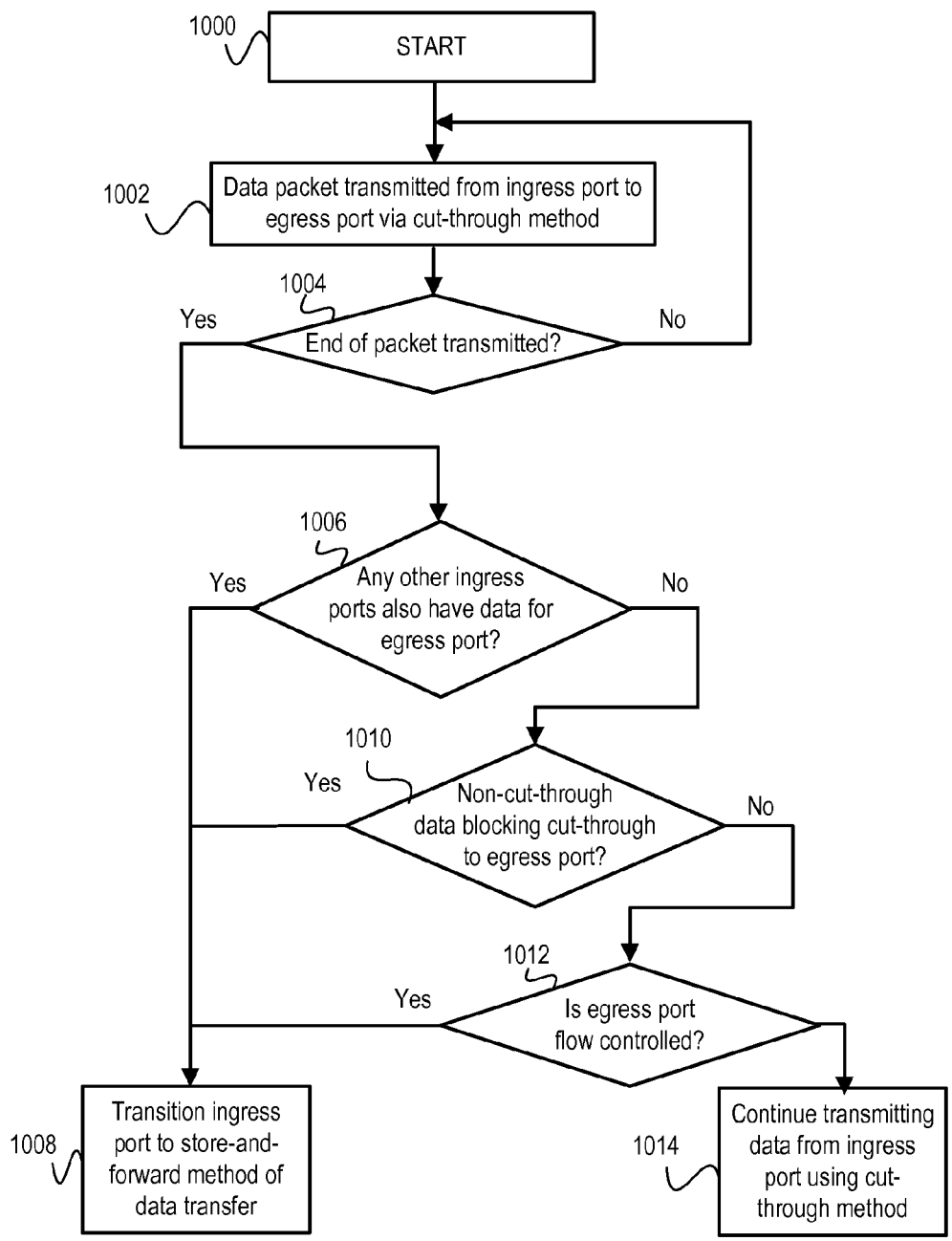
FIG. 10 is a flow diagram of an exemplary logic for transferring data.

FIG. 10 shows example logic of how an ingress port transmitting data according to cut-through to an egress port may determine whether or not to continue to transmit data according to cut-through, or to transition to a different data transfer type, such as store-and-forward. The logic of FIG. 10 may be performed, for example, by one or more controllers or control modules of one or more ingress nodes. The logic of FIG. 10 may be used when an ingress port is presently transmitting a data packet to an egress port, and has at least one additional data packet or set of data to transmit to the egress port after the present data packet.

The logic may begin at block 1000. At block 1002, a data packet may be transmitted from the ingress port to the egress port via or according to a cut-through data transfer. The data packet may be transmitted to the egress port by ingress port, which may be one of the ingress ports of an ingress node of the system.

At block 1004, the system may determine whether an end of packet associated with the data packet transmitted in 1002 has been received. In some variations, the system may determine whether the transmission of the data packet has finished. If it has not, the logic may return to block 1002 and the data packet may continue to be transmitted to the egress port.

If the end of packet for the data packet has been received at block 1004, the logic may proceed to block 1006. The ingress port may have another data packet to send to the egress port. In block 1006, the system may determine whether any other ingress port of the system also have data for egress port. If at least one other ingress port also has data for the egress port, the logic may proceed to block 1008, where the ingress port may transition from transmitting data through cut-through to transmitting data through store-and-forward, or some other data transfer type.

If no ingress ports other than the ingress port have data for the egress port, the logic may proceed to block 1010. At block 1010, the system may determine whether there is any non-cut-through data present that is blocking cut-through to the egress port. In many systems, the determination at block 1010 should be that there is not any non-cut-through data present that is blocking cut-through to the egress port, as the egress port was just receiving cut-through data from the ingress port. However, if non-cut-through data is present that is blocking cut-through to the egress port, the logic may proceed to block 1008, and the ingress node may transition to transmitting data using store-and-forward.

If no non-cut-through data is present that is blocking cut-through to the egress port, the logic may proceed to block 1012. At block 1012, the system may determine whether the egress port is flow controlled. If the egress port is flow controlled, the logic may proceed to block 1008, and the ingress port may transition to transmitting data using a store-and-forward data transfer.

Block 1012 may resemble or otherwise function in a manner similar to block 916. The determination at block 1012 may be made depending on a class of service or priority level associated with the data to be sent to the egress port. The data received may be associated with one of a number of class of services, and the destination egress port may be flow controlled for some class of services and not for others. The system may, for example, use an egress cut-through statement vector that includes values for each egress port and class of service to make the determination, such as an egress cut-through statement vector that contains a bit per egress port-class of service pair.

If the egress port is not flow controlled, the logic may proceed to block 1014. At block 1014, the ingress port may continue to transmit data to the egress port using the cut-through data transfer. In this situation, the ingress port may begin sending the next data packet or set of data to the egress port using the cut-through data transfer type. In such systems, the logic may return to block 1002.

In some variations, the logic of FIG. 10 may include fewer or more blocks or functions. In some implementations, one or more blocks may perform different functions. Additionally or alternatively, one or more blocks may be combined into fewer functions or determinations. Additionally or alternatively, one or more blocks or functions may be performed in a different order or at the same time. Various other examples and variations are possible.

In some systems, a guard band may be implemented to allow for a longer delay or wait before ingress nodes make a cut-through decision. The guard band may be a configurable delay period which may be longer than actually needed, and may ensure that the cut-through decisions performed by the ingress nodes are performed after all cut-through statement vectors should have been received. The guard band may ensure a robust design with respect to process variations and unexpected design flaws. Other systems may not include a guard band.

In the logic of FIG. 8, cut-through decisions may be made every clock cycle. A reduction in some costs may be achieved by performing cut-through decisions less frequently. For example, a portion of data and cut-through statement vectors may be sent during one clock cycle, while a second portion of the data and cut-through statement vectors may be sent during the next clock cycle. In this way, only half of the wiring between tiles or nodes of the system may be needed, as first data and cut-through statement vectors may be sent during the first clock cycle over the same wires as second data and cut-through statement vectors that are sent during the next clock cycles. Wiring costs may be further reduced by increasing the number of clock cycles used to transmit the data and cut-through statement vectors. Other variations are possible.

The systems described may be useful for creating and transmitting cut-through statement vectors to ingress nodes of a system. With these cut-through statement vectors, the ingress nodes may be delivered all information necessary to determine whether or not data may be sent to an egress port using a cut-through data transfer. Ingress nodes may run one or more algorithms or functions to determine, based on the cut-through statement vectors of the other ingress nodes and of the relevant egress port, whether an egress port is capable or available to receive data from an ingress port using a cut-through data transfer, and/or whether the ingress node is authorized to transfer the data using cut-through. These algorithms or functions may be run in parallel on ingress nodes at or near the same time. Using cut-through statement vectors effectively may allow for a collision-free cut-through decision to be made by the ingress nodes independently. These systems may significantly reduce computational time of a system, and may allow for data to be transferred through a system 105 more quickly and efficiently. These systems may provide minimal latency for a collision free cut-through algorithm. Algorithmic delays may be isolated to the one-way propagation delay of state information, and may avoid two-way delay associated with a centralized arbiter or "request-grant" algorithms. These systems may provide a useful distributed functionality for cloud processing, financial sectors, and social networking, where low latency and high bandwidth may be needed and useful to drive revenue. These systems may coordinate data transfers using cut-through for multiple ingress nodes based on a state of an egress port.

The devices and logic described above, such as the ingress nodes or ports, egress nodes or ports, and/or controllers or control modules of ingress or egress nodes or ports, may be implemented in many different ways in many different combinations of hardware, software or both hardware and software. For example, all or parts of the system may include circuitry in a controller, a microprocessor, or an application specific integrated circuit (ASIC), or may be implemented with discrete logic or components, or a combination of other types of analog or digital circuitry, combined on a single integrated circuit or distributed among multiple integrated circuits. All or part of the logic described above may be implemented as instructions for execution by a processor, controller, or other processing device and may be stored in a tangible or non-transitory machine-readable or computer-readable medium such as flash memory, random access memory (RAM) or read only memory (ROM), erasable programmable read only memory (EPROM) or other machine-readable medium such as a compact disc read only memory (CDROM), or magnetic or optical disk. Thus, a product, such as a computer program product, may include a storage medium and computer readable instructions stored on the medium, which when executed in an endpoint, computer system, or other device, cause the device to perform operations according to any of the description above.

The processing capability of the system may be distributed among multiple system components, such as among multiple processors and memories, optionally including multiple distributed processing systems. Parameters, databases, and other data structures may be separately stored and managed, may be incorporated into a single memory or database, may be logically and physically organized in many different ways, and may implemented in many ways, including data structures such as linked lists, hash tables, or implicit storage mechanisms. Programs may be parts (e.g., subroutines) of a single program, separate programs, distributed across several memories and processors, or implemented in many different ways, such as in a library, such as a shared library (e.g., a dynamic link library (DLL)). The DLL, for example, may store code that performs any of the system processing described above.

While various embodiments of the invention have been described, it will be apparent to those of ordinary skill in the art that many more embodiments and implementations are possible within the scope of the invention. Accordingly, the invention is not to be restricted except in light of the attached claims and their equivalents.

What is claimed is:

1. A system for transferring data, comprising:
an egress node including an egress port;
an ingress node configured to receive a data segment of a data packet destined for the egress port, the data packet associated with a packet priority level;
where the ingress node is configured to receive an egress statement vector from the egress node, the egress statement vector indicates whether the egress port is or is not flow controlled for data associated with the packet priority level; and
where the ingress node is configured to determine whether the egress port is available to receive the data segment from the ingress node before other data segments of the data packet are received at the ingress node based on the egress statement vector and based on a comparison of the packet priority level with an egress entry of the egress statement vector corresponding to the packet priority level.

2. The system of claim 1, where the egress port is not available to receive the data segment from the ingress node before the other data segments of the data packet are received at the ingress node when the egress statement vector indicates that the egress port is flow controlled for data associated with the packet priority level.

3. The system of claim 1, where the egress port is available to receive the data segment from the ingress node before the other data segments of the data packet are received at the ingress node when the egress statement vector indicates that the egress port is not flow controlled for data associated with the packet priority level.

4. The system of claim 1, where the ingress node is configured to store the data segment in a memory in communication with the ingress node when the egress statement vector indicates that the egress port is flow controlled for data associated with the packet priority level.

5. The system of claim 1, where the ingress node is configured to bypass memory and transmit the data segment directly to the egress port when the egress statement vector indicates that the egress port is not flow controlled for data associated with the packet priority level.

6. The system of claim 1, where the egress statement vector includes a first entry indicating that the egress port is flow controlled for data associated with a first priority level, and a second entry indicating that the egress port is not flow controlled for data associated with a second priority level; and
where the packet priority level is the first priority level or the second priority level.

7. The system of claim 1, where the ingress node is configured to receive an ingress statement vector from a second ingress node, the ingress statement vector indicating whether the second ingress node includes data associated with the packet priority level for the egress port.

8. The system of claim 7, where the determination further includes:
comparison of the packet priority level with an ingress entry of the ingress statement vector corresponding to the packet priority level.

9. The system of claim 1, where the egress statement vector from the egress node further indicates a level of congestion at the egress port.

10. A method for transferring data, comprising:
receiving, at a receiving ingress node, a data segment of a data packet destined for an egress port of an egress node, the data packet associated with a packet priority level;
identifying, at the receiving ingress node, an egress statement vector from the egress node, the egress statement vector indicating whether the egress port is or is not flow controlled for data associated with the packet priority level; and
storing the data segment in a memory until all data segments of the data packet have been received at the receiving ingress node when the egress statement vector indicates that the egress port is flow controlled for data associated with the packet priority level.

11. The method of claim 10, further comprising receiving, at the receiving ingress node, an ingress statement vector indicating whether an non-receiving ingress node includes data associated with the packet priority level for the egress port.

12. The method of claim 11, further comprising determining, at the receiving ingress node, whether the receiving ingress node is available to transfer the data segment to the egress port before other data segments of the data packet are received at the receiving ingress node, the determination based on the egress statement vector and the ingress statement vector.

13. The method of claim 12, further comprising transferring the data segment to the egress port before other data segments of the data packet are received at the receiving ingress node when the egress statement vector indicates that the egress port is not flow controlled for the packet priority level and the ingress statement vector indicates that the non-receiving ingress node does not have data associated with the packet priority level for the egress port.

14. The method of claim 12, further comprising storing the data segment until all other data segments of the data packet are received at the receiving ingress node when the ingress statement vector indicates that the non-receiving ingress node has data associated with the packet priority level for the egress port.

15. An ingress node of a system, comprising:
an ingress port;
a memory in communication with the ingress port, the ingress port configured to receive a data segment of a data packet destined for an egress port of an egress node, the data segment associated with a packet priority level;
a controller in communication with the memory and the ingress port, the controller operable to receive an egress statement vector from the egress node indicating whether the egress port is flow controlled for data associated with a first priority level and whether the egress port is flow controlled for data associated with a second priority level, wherein the egress port being flow controlled indicates availability of the egress port to receive the data segment without the data segment being stored in memory; and the controller operable to determine, based on the packet priority level and the egress statement vector, whether the egress port is available to receive the data segment from the ingress node without first storing the data segment in memory.

16. The ingress node of claim 15, where the memory comprises:

a first queue configured to store data associated with the first priority level when the egress port is flow controlled for data associated with the first priority level; and a second queue configured to store data associated with the second priority level when the egress port is flow controlled for data associated with the second priority level.

17. The ingress node of claim 15, where the controller is further operable to instruct the ingress port to bypass the memory and transmit the data segment directly to the egress port when the egress port is available.

18. The ingress node of claim 15, where the controller is further operable to store the data segment in the memory when the egress port is not available.

19. The ingress node of claim 15, where the controller is further operable to:

identify the packet priority level as the first priority level or the second priority level; and determine the egress port is available based on an entry in the egress statement vector corresponding to the identified packet priority level, the entry indicating the egress port is flow controlled for data associated with the identified packet priority level.

20. The ingress node of claim 15, where the packet priority level may be one of a set of priority levels, the set of priority levels including the first priority level and the second priority level; and where the egress statement vector includes a set of entries indicating whether the egress port is flow controlled for data associated with each of the priority levels.

* * * * *